United States Patent
Sherry et al.

(10) Patent No.: US 6,221,071 B1
(45) Date of Patent: Apr. 24, 2001

(54) RAPID ELECTRODE DEPLOYMENT

(75) Inventors: John Sherry, Needham, MA (US); Keith Hoffman, Spencer, IN (US)

(73) Assignee: SCIMED Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/326,751

(22) Filed: Jun. 4, 1999

(51) Int. Cl.$^7$ .................................................. A61B 18/14
(52) U.S. Cl. ................................ 606/41; 607/99; 607/113
(58) Field of Search ..................... 606/41; 607/99, 607/105, 113; 600/374

(56) References Cited

U.S. PATENT DOCUMENTS

| | | |
|---|---|---|
| 4,989,614 | 2/1991 | Dejter et al. . |
| 5,361,760 * | 11/1994 | Normann et al. ................ 128/642 |
| 5,368,045 | 11/1994 | Clement et al. . |
| 5,526,822 | 6/1996 | Burbank et al. . |
| 5,649,547 | 7/1997 | Ritchart et al. . |
| 5,667,488 | 9/1997 | Lundquist et al. . |
| 5,769,086 | 6/1998 | Ritchart et al. . |
| 5,775,333 | 7/1998 | Burbank et al. . |
| 5,794,626 | 8/1998 | Kieturakis . |
| 5,803,912 | 9/1998 | Siczek et al. . |
| 5,827,276 | 10/1998 | LeVeen et al. . |
| 5,836,906 * | 11/1998 | Edwards ............................... 604/22 |
| 5,980,517 * | 11/1999 | Gough .................................. 606/41 |
| 6,050,992 * | 4/2000 | Nichols ................................ 606/41 |
| 6,053,937 * | 4/2000 | Edwards et al. ................... 607/104 |
| 6,071,280 * | 6/2000 | Edwards et al. ..................... 606/41 |

FOREIGN PATENT DOCUMENTS

| | | |
|---|---|---|
| 2323283A | 9/1998 | (GB) . |
| WO92/10142 | 6/1992 | (WO) . |
| WO96/29946 | 10/1996 | (WO) . |
| WO98/06334 | 2/1998 | (WO) . |
| WO98/49943 | 11/1998 | (WO) . |

* cited by examiner

*Primary Examiner*—Lee Cohen
(74) *Attorney, Agent, or Firm*—Testa, Hurwitz & Thibeault, LLP

(57) ABSTRACT

An apparatus for ablating tissue has an elongate member, at least two electrodes housed within an axial lumen of the elongate member, and an electrode actuator for advancing the electrodes beyond a distal end of the elongate member and into tissue to a site targeted for ablation. The electrode actuator rapidly advances the electrodes beyond the distal end of the elongate member so that the electrodes assume a uniform outwardly everted configuration.

3 Claims, 10 Drawing Sheets

RAPID ELECTRODE DEPLOYMENT

TECHNICAL FIELD

The invention relates generally to apparatus and methods for tissue ablation. More particularly, the invention relates to the rapid deployment of an everted array of electrodes used to ablate tissue.

BACKGROUND INFORMATION

Many of the current procedures for the treatment of cancer are disruptive and cause damage to healthy tissue. Two such procedures include resection of the tumor and hyperthermia treatment of the tumor. In a resection procedure, the physician must be careful not to cut the tumor in a manner that creates seeding of the tumor and thereby results in metastasis. In a hyperthermia procedure, the extent of localization of the heat is generally poor, resulting in damage to healthy tissue in the vicinity of the treatment site.

Ablation of cellular tissues in situ is used to treat cancer in a manner that ideally minimizes both the potential for damage to healthy tissue and for seeding of the tumor cells. Ablative procedures deliver electromagnetic energy directly to the tumor cells so as to necrose the tumor cells. The tumor cells are not cut, so the incidence of seeding is eliminated. Furthermore, the use of electromagnetic energy can be advantageous, because it can be rapidly dissipated and therefore can reduce the incidence of damage to healthy tissue surrounding the treatment site.

One such electromagnetic energy for use in ablation of tumor cells is radio frequency, or RF, energy. In typical RF ablation procedures, however, it is difficult to position the ablation electrodes so as to ablate effectively the entire tumor mass without resorting to multiple procedures.

SUMMARY OF THE INVENTION

An everted array of ablation electrodes can be used in an attempt to ablate effectively the largest possible volume of tissue mass during each ablation procedure. U.S. Pat. No. 5,827,279, which is hereby incorporated by reference herein, relates to this type of electrode array. Such everted arrays of electrodes can be difficult to deploy accurately and uniformly into tissue. The individual electrodes of the array can become bent or twisted as they enter the tissue and therefore do not develop a uniform shape. Without this uniform shape, the largest possible volume of the tumor is typically not treated during each procedure. Additionally, such everted arrays may not deploy accurately in that the electrodes can push against the tumor and move it, rather than penetrate it.

It is an object of the invention to reduce the difficulties associated with accurate and uniform deployment of an everted array of electrodes into tissue for the ablation of tumors. It is another object of the invention to provide an apparatus for tissue ablation that includes an electrode actuator to advance rapidly electrodes into tissue so that they assume an outwardly everted configuration within the tissue and thereby increase the volume of tissue treated by the electrodes in a single ablation procedure. An outwardly everted configuration is intended to include a configuration of the electrode array in which substantially all of the individual electrodes of the at least two electrodes in the array extend from the distal end of the elongate member and curve back toward the elongate member without otherwise bending or twisting.

The invention relates to an apparatus for tissue ablation which comprises an elongate member, at least two electrodes, and an electrode actuator. The elongate member has a proximal end, a distal end, and a lumen. The electrodes are housed within the lumen of the elongate member, and the electrodes are advanceable beyond the distal end of the elongate member and into tissue to a target site. The electrode actuator operates to advance rapidly the electrodes beyond the distal end of the elongate member and into tissue to the target site. The rapid advancement of the electrodes prevents the electrodes from bending or twisting as they enter the tissue, thereby allowing them to assume an outwardly everted configuration as they are advanced into the tissue.

The external surface of the elongate member can be at least partially insulated by, for example, being covered with an insulating material. Alternatively, all but the distal end of the external surface of the elongate member can be covered with an insulating material. In another embodiment, the distal end of the elongate member comprises a sharpened tip for penetrating tissue. In some embodiments in which the elongate member has a sharpened tip, the tissue ablation apparatus can further comprise an elongate member actuator, which operates to advance rapidly the elongate member so that the sharpened tip penetrates tissue at the target site.

The electrodes may be needle electrodes. The electrodes may also be at least partially covered with an insulating material. In one embodiment, the electrodes are hollow needle electrodes in communication with a fluid reservoir for delivering a fluid to the target site. After advancement of the electrodes beyond the distal end of the elongate member, the electrodes may be retracted back into the lumen of the elongate member. In one embodiment of the invention, the electrodes are in electrical communication with a source of RF energy and deliver RF energy to the target site so as to ablate tissue at the target site. In another embodiment, the electrodes are in electrical communication with an impedance monitor for monitoring an impedance of tissue at the target site.

An electrode actuator for use in an apparatus of the invention may be any device capable of exerting a force on the electrodes so as to advance rapidly the electrodes beyond the distal end of the elongate member and into tissue while assuming a uniform outwardly everted configuration. The electrode actuator may comprise a spring or a pneumatic cylinder, such as a carbon dioxide ($CO_2$) cylinder. Additionally, an elongate member actuator according to the invention may be any device capable of exerting a force on the elongate member so as to advance rapidly a sharpened tip of the elongate member into tissue at a target site. The elongate member actuator may comprise a spring, for example.

Methods of the invention relate to the use of an apparatus, such as the above-described apparatus, to ablate tissue. In some embodiments, the sharpened distal tip of the elongate member is used to advance, rapidly or not, the tip of the apparatus to the target site. The target site within tissue generally is the site of a tumor or any other tissue mass targeted for ablation. The electrodes are then rapidly advanced into the tissue to the target site so that they assume an outwardly everted configuration, as described above. The tissue at the target site is then ablated (by, for example, delivering RF energy to the target site via the electrodes). The impedance of tissue at the target site can be monitored and fluid can be delivered to the target site. The measured impedance and the delivery of fluid can be used either separately or together to control the course of the ablation and to achieve the desired result.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Apparatus and methods are provided for the ablation of tissue at a target site. The target site can be a site of a tumor within the tissue of a patient's body or any other site within the tissue that is selected for ablation. An apparatus according to the invention includes an elongate member, at least two electrodes, and an electrode actuator. The elongate member has a proximal end, a distal end, and a lumen. The elongate member also has a sharpened tip at its distal end for penetrating tissue. Housed within the elongate member are the electrodes, which may be advanced beyond the distal end of the elongate member and into tissue to the target site. The electrodes may also be retracted back into the elongate member from the advanced state. The electrode actuator operates to advance rapidly the electrodes beyond the distal end of the elongate member and into tissue to the target site. The electrode actuator may be any of a variety of devices capable of exerting a force on the electrodes so as to advance rapidly the electrodes beyond the distal end of the elongate member and into tissue such that the electrodes form an outwardly everted configuration at the target site within the tissue. The electrode actuator can be, for example, a spring or a pneumatic cylinder, such as a $CO_2$ cylinder.

Methods of the invention provide for inserting an apparatus, such as the above-described apparatus, into tissue to the target site by penetrating the tissue with the sharpened distal end of the elongate member, rapidly advancing the electrodes from the distal end of the elongate member and into tissue at the target site, and ablating tissue at the target site. The electrodes are rapidly advanced so that they assume an outwardly everted configuration in the tissue at the target site. An outwardly everted configuration is intended to include a configuration of the electrode array in which substantially all of the individual electrodes extend from the distal end of the elongate member and curve back toward the elongate member without otherwise bending or twisting.

Figure 1:
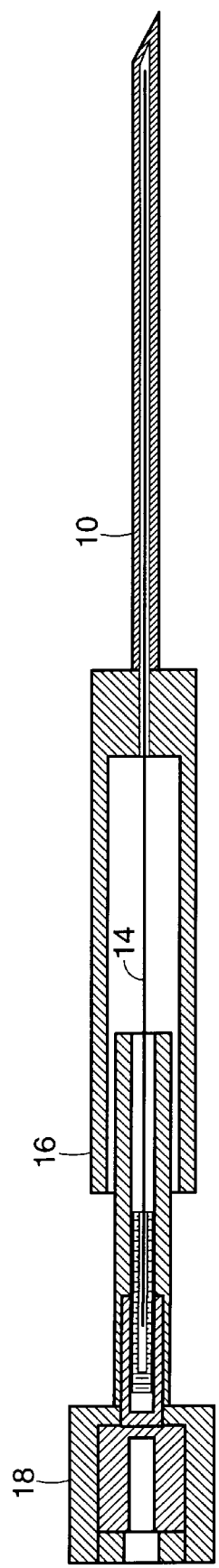
FIG. 1 is an illustration of a device for use in tissue ablation which, when combined with an actuator, forms an apparatus of the invention.

FIG. 1 is an illustration of a device for use in tissue ablation, which forms a component of an apparatus of the invention. The device shown in FIG. 1 is used in conjunction with an electrode actuator to form an apparatus of the invention. The device of FIG. 1 includes an elongate member 10, an electrode bundle 14, a housing 16, and a plunger 18. The elongate member 10 has a sharpened tip 12 at its distal end and an axial lumen. In one embodiment, the elongate member 10 is a hollow stainless steel shaft. In another embodiment, the external surface of the elongate member 10 is at least partially covered with an insulating material. The insulating material may, for example, cover all but 1 cm of the distal end of the elongate member. The insulating material includes, but is not limited to, polyester, teflon, and epoxy papalene wax.

In the illustration of FIG. 1, the electrodes of the electrode bundle 14 are shown in their undeployed state. An electrode bundle 14 contains at least two electrodes. In FIG. 1, the electrode bundle 14 is shown housed within the axial lumen of the elongate member 10. While the electrode bundle 14 is in its undeployed state, as in FIG. 1, the individual electrodes are constrained by the elongate member 10 in a collapsed configuration.

Figure 2A:
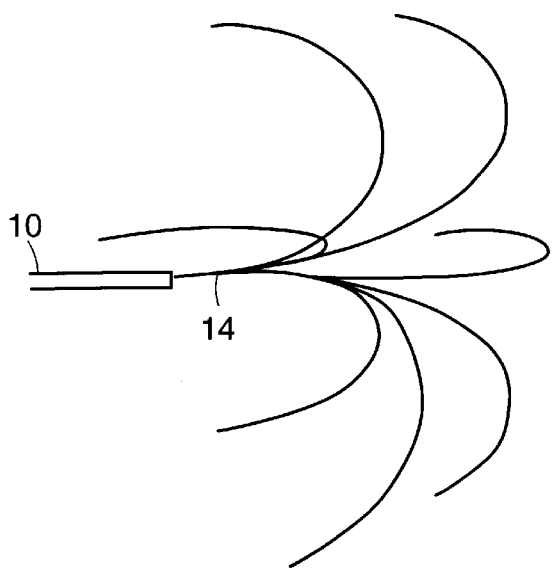
FIG. 2A is an illustration of an outwardly everted electrode array.
Figure 2B:
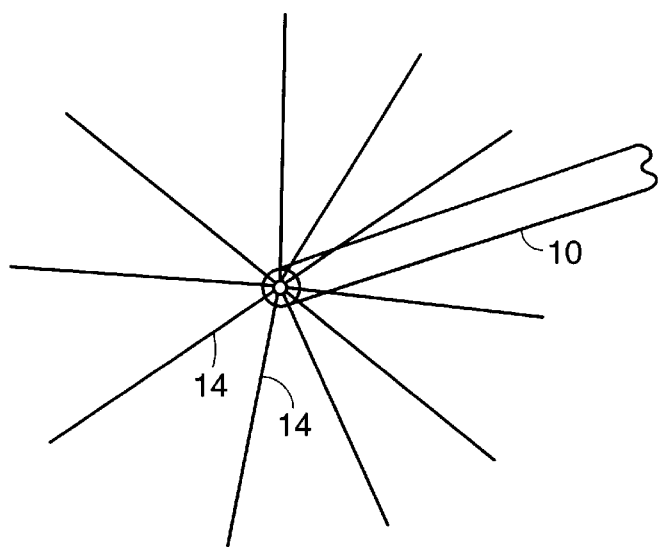
FIG. 2B is an illustration of another view of an outwardly everted electrode array.

The electrodes of the electrode bundle 14 are formed from a conductive or semi-conductive metal that has a shape memory. Such conductive metals having shape memory include, but are not limited to, stainless steel, nickel-titanium alloys, and spring steel alloys. The metal may be formed into wires. When rapidly deployed beyond the distal end of elongate member 10 and into tissue, the shape memory of the individual electrodes, along with the rapid deployment, allows the electrodes to deflect into the everted three-dimensional configuration shown in FIG. 2A. In this figure, the electrodes of the electrode bundle 14 are shown advanced beyond the distal end of the elongate member 10. Other configurations of the electrodes besides the everted array shown in FIG. 2A may be possible and are intended to be included within the scope of the invention. A perspective view of the electrode configuration is shown in FIG. 2B. The electrodes of the electrode bundle 14 are preferably symmetrically positioned about the axis of the elongate member 10. The individual electrodes of the electrode bundle 14 may be joined using an epoxy, weld, etc., to provide maximum column strength to the electrode bundle 14.

Figure 3:
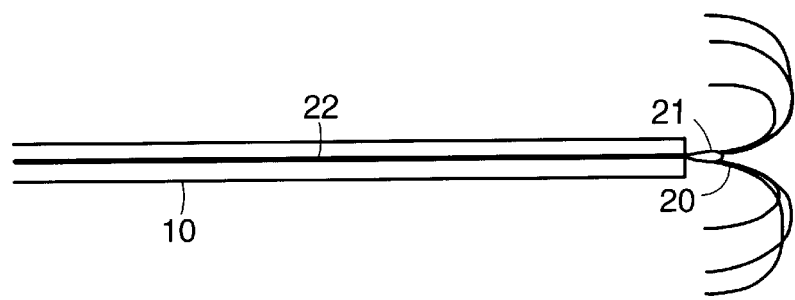
FIG. 3 is an illustration in which the individual electrodes of an outwardly everted electrode array are attached to the end of a rod.

In an alternative embodiment, shown in FIG. 3, a plurality of electrodes 20 are connected at the end of a rod 22 near the distal end of elongate member 10, rather than in an electrode bundle. The plurality of electrodes 20 are, for example, soldered to the distal end of the rod 22 at solder joint 21. This solder joint 21 generally increases the bulk of the rod 22 and electrodes 20.

Figure 4A:
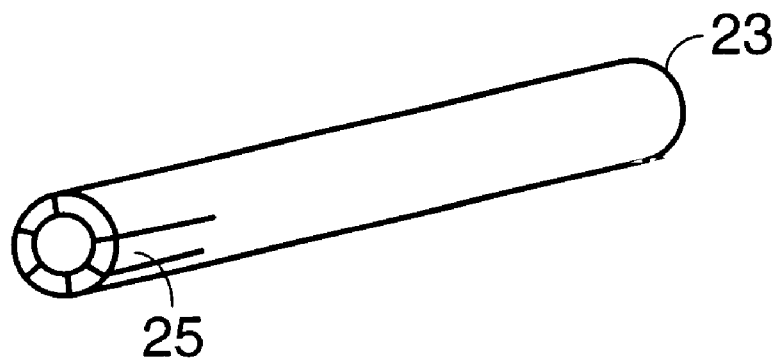
FIG. 4A is an illustration of the distal end of a metal rod from which an everting array of electrodes may be cut.
Figure 4B:
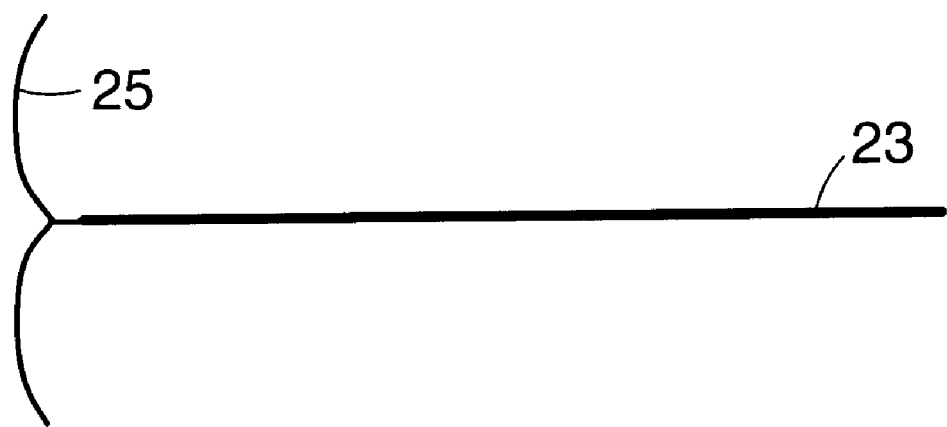
FIG. 4B is an illustration of an everting array of electrodes cut from the distal end of the rod in FIG. 4B.

In another embodiment, the individual electrodes are not contained in an electrode bundle or soldered at the end of a rod, but are cut from a hypotube or metal rod. A metal rod 23 such as the one shown in FIG. 4A may, for example, be laser cut. For example, a 0.050" rod 23 can be laser cut using a pulsed laser at the distal end so as to cut fingers 25 in the distal end of the rod 23. These fingers 25 can then be formed into the everting array, as shown in FIG. 4B, by applying cold-work through bending and coining operations (e.g., in the case of stainless steel) or through bending and heat treatment operations (e.g., in the case of nickel-titanium alloys).

This needle design, as well as the design using an electrode bundle, allows for a smaller gauge elongate member to be used in an apparatus of the invention. For example, if a needle array such as that shown in FIG. 3 is used, a 15 gauge or larger elongate member is generally required for an array of eight 3.0 cm needles. An array comprising a bundle of needle electrodes or an array comprising needles cut from a metal tube would allow for a smaller gauge elongate member to be used since the bulk of the solder joint can then be avoided.

In one embodiment, the individual electrodes of the electrode bundle 14 are needle electrodes. In another embodiment, the electrodes are hollow. These hollow needle electrodes may be in communication with a fluid reservoir for delivery of fluid to the target site. The fluid may include saline, or any other biologically compatible fluid, or it may include a chemotherapeutic agent, for example. In still another embodiment, the individual electrodes of the electrode bundle 14 are at least partially covered with an insulating material, such as polyester, teflon, etc.

Figure 5A:
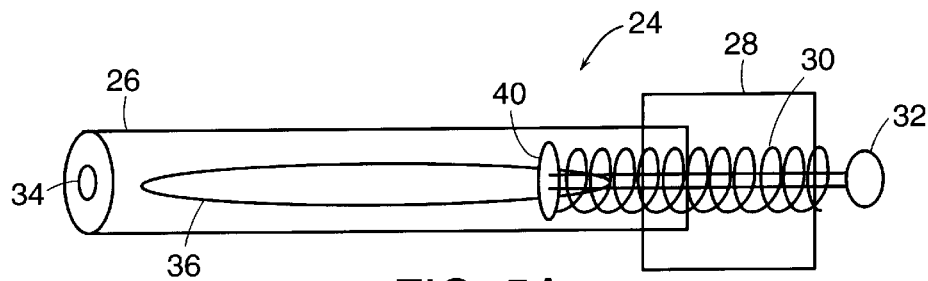
FIG. 5A is an illustration of a spring electrode actuator of the apparatus of the invention in its unarmed state.
Figure 6A:
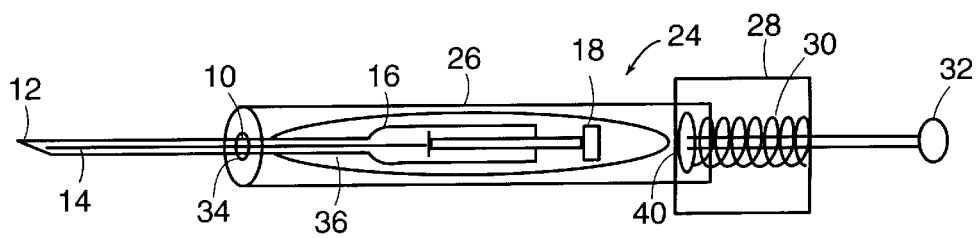
FIG. 6A is an illustration of an apparatus of the invention with the spring electrode actuator and the electrodes in their undeployed state.

A spring electrode actuator 24 is shown in FIG. 5A. The spring electrode actuator 24 for use in an apparatus of the invention includes a cannula 26, a cap 28, a spring 30, and a spring pin 32. The cannula 24 has an axial lumen and an opening 34 at its distal end. The opening 34 is large enough to permit the passage of the elongate member 10 of the device shown in FIG. 1, but not the housing 16. The axial lumen of the cannula 24 is large enough to accommodate the housing 16, as is shown in FIG. 6A. An apparatus of the invention therefore includes a device, as shown in FIG. 1, in conjunction with an electrode actuator, as shown in FIG. 6A. The cannula 24 also contains power supply connection opening 36 through which the electrodes of the electrode bundle 14 are connected to a source of energy (discussed in further detail below in connection with FIG. 10).

Figure 5B:
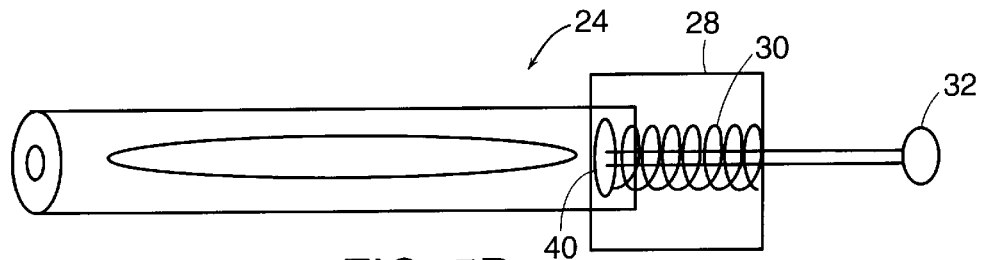
FIG. 5B is an illustration of the spring electrode actuator of FIG. 5A in its armed state.
Figure 5C:
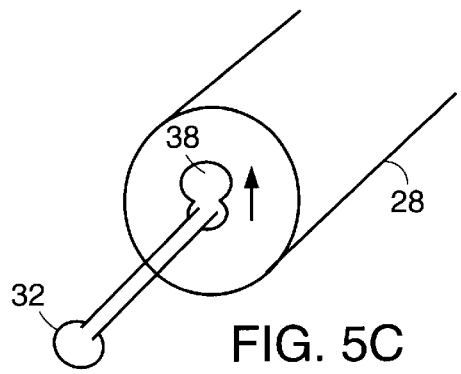
FIG. 5C is an illustration of the spring electrode actuator of FIGS. 5A and 5B in its armed state as viewed from its proximal end.

In the illustration of the electrode actuator 24 shown in FIG. 5A, the electrode actuator is not armed. FIG. 5B is an illustration of the electrode actuator 24 in its armed state. The cap 28 contains a locking hole 38 at its proximal end, as shown in FIG. 5C. The locking hole 38 has two different diameters, so that the spring pin 32 may be locked into the armed position, as shown in FIG. 5C. In operation, the spring pin 32 is pulled away from the cap 28 so as to create tension on the spring 30, and then the spring pin 32 is forced into the smaller of the two diameters of locking hole 38 so as to lock the spring pin 32 into place. To fire the electrode actuator 24, the spring pin 32 is moved into the larger of the two diameters of the locking hole 38 so as to release the tension on the spring 30.

Figure 6B:
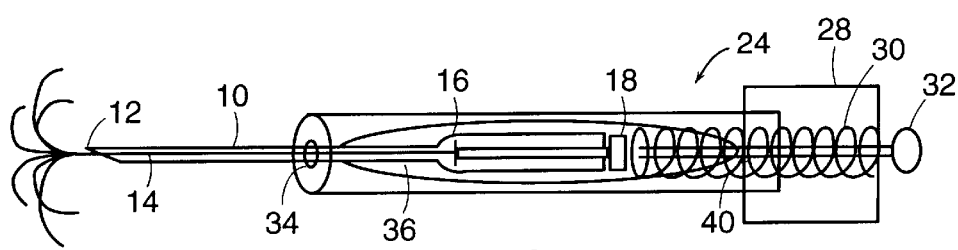
FIG. 6B is an illustration of the apparatus of FIG. 6A with the spring electrode actuator and the electrodes in their deployed state.

FIG. 6A is an illustration of an apparatus of the invention with a spring electrode actuator 24. Potential energy from the spring 30 of the electrode actuator 24 is used to advance rapidly the electrodes of the electrode bundle 14 from the distal end of the elongate member 10. In operation, tension is created on the spring 30, as described above, and then released, also as described above, so that the energy from the spring 30 rapidly advances the electrodes of the electrode bundle 14 from the distal end of the elongate member 10. Upon release of spring tension, the disc 40, attached to the distal end of the spring pin 32, strikes the plunger 18 and thereby rapidly advances the electrodes of the electrode bundle 14 beyond the distal end of the elongate member 10, as shown in FIG. 6B. The electrodes of the electrode bundle 14 may be retracted back into the elongate member 10, by, for example, pulling the plunger 18 away from the housing 16.

Figure 7A:
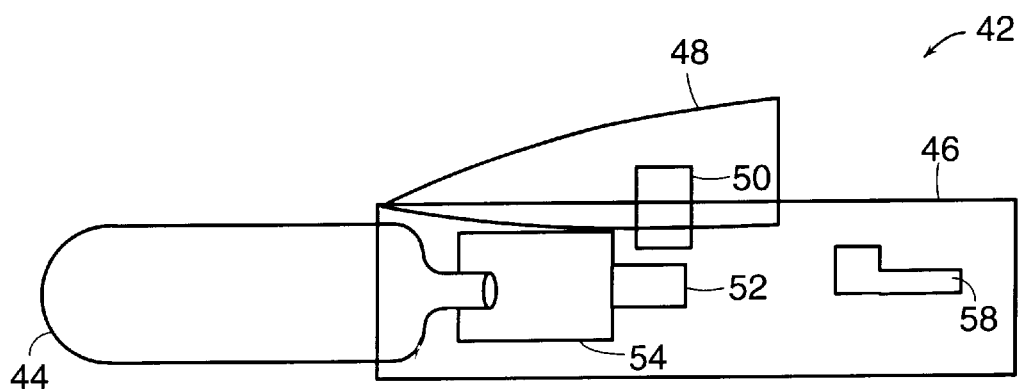
FIG. 7A is an illustration of a pneumatic cylinder electrode actuator of the invention.
Figure 7B:
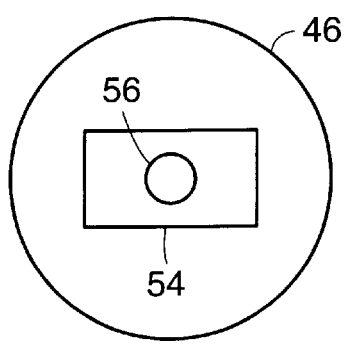
FIG. 7B is an illustration of the pneumatic cylinder electrode actuator of FIG. 7A as viewed from its proximal end.

FIG. 7A is an illustration of a pneumatic cylinder electrode actuator 42. The electrode actuator 42 includes a pneumatic cylinder 44, a cannula 46, an actuation plate 48, a pin 50, a valve 52, and a housing 54 within the cannula 46. Also shown in FIG. 7A is power connection opening 58 for use in connecting a source of energy to the electrodes of electrode bundle 14. The housing 54 includes a threaded opening 56 for receiving the pneumatic cylinder 44, as shown in FIG. 7B. In operation, the actuation plate 48 is squeezed toward the cannula 46 so as to press the pin 50 down. The pin 50 then opens the valve 52, thereby releasing the gas pressure inside the cylinder 44.

Figure 8:
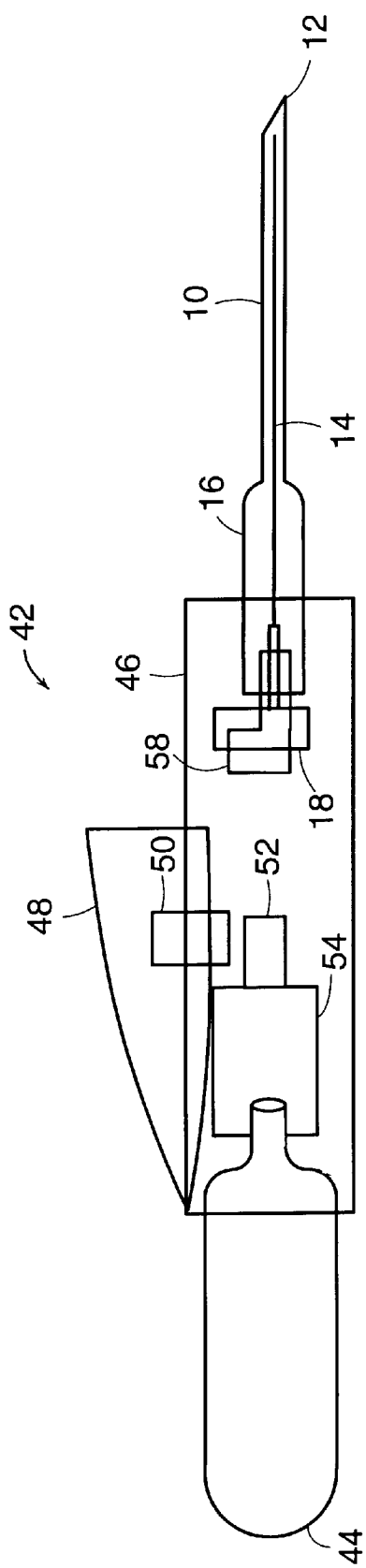
FIG. 8 is an illustration of an apparatus of the invention with the pneumatic electrode actuator and the electrodes in their undeployed state.

FIG. 8 is an illustration of an apparatus of the invention with the pneumatic cylinder electrode actuator 42. When pressure from the cylinder 44 is released as described above, the pressure acts on the plunger 18 so as to advance the electrodes of electrode bundle 14 beyond the distal end of the elongate member 10. The electrodes of the electrode bundle 14 may be retracted back into the elongate member 10, by, for example, pulling the plunger 18 away from the housing 16.

In alternative embodiments, other devices for generating a force on the electrodes of the electrode bundle 14 may also be used to advance rapidly the electrodes. Such devices include, but are not limited to, motors, rubber bands, hydraulics, levers, lever and hammer configurations, and combustion/explosion devices. As used herein, "rapidly" means that the electrodes of the electrode bundle 14 are advanced at a rate of between about 30 cm/s and about $10^5$ cm/s.

Figure 9A:
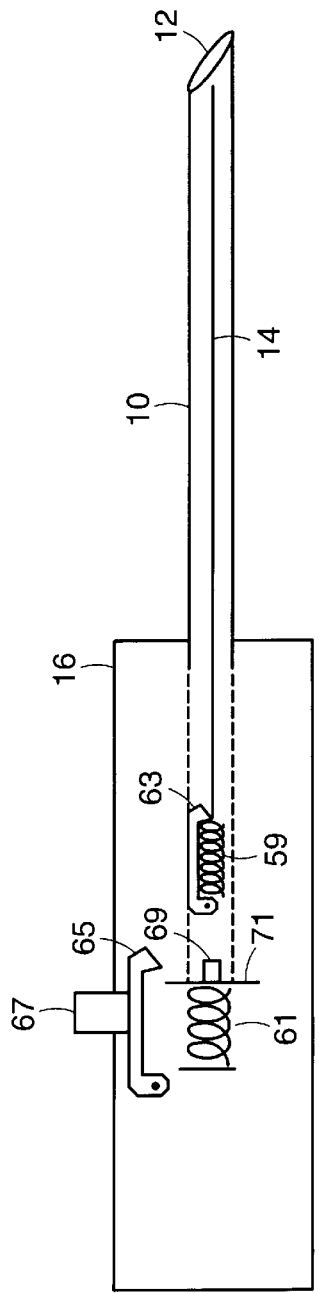
FIG. 9A is an illustration of an apparatus of the invention with both a spring electrode actuator and a spring elongate member actuator in its armed state.
Figure 9B:
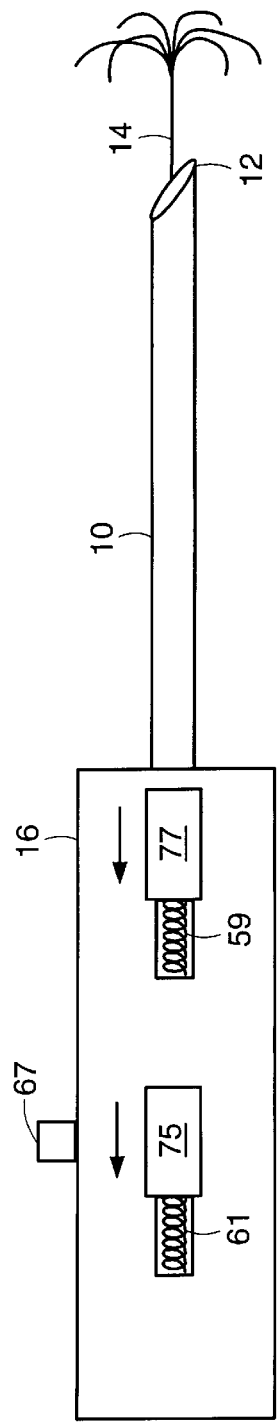
FIG. 9B is a top view of the apparatus of FIG. 9A showing slide tabs for creating tension on the spring actuators.
Figure 9C:
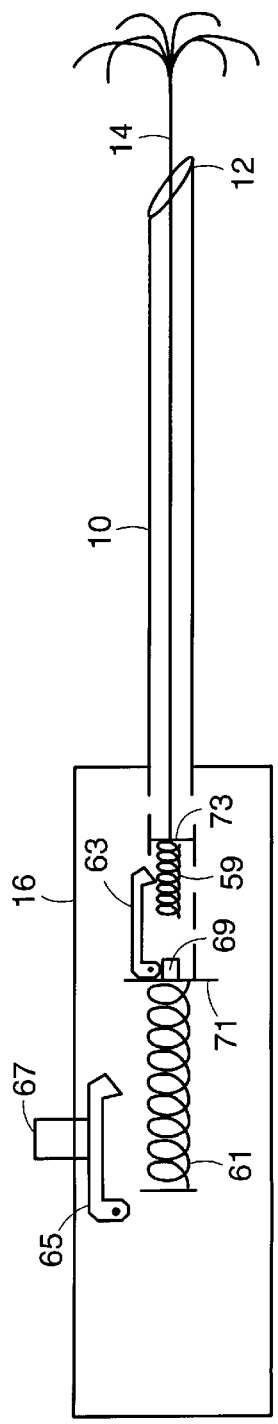
FIG. 9C is an illustration of the apparatus of FIG. 9A in its unarmed state with the electrodes deployed.

An alternative embodiment of the invention that includes both an electrode actuator and an elongate member actuator is shown in FIGS. 9A–9C. When attempting to advance manually the sharpened tip 12 of an apparatus for ablation into dense, fibrous tumors, such as breast tumors, the tumor mass may move relative to the tip 12. It may, therefore, also be advantageous to advance the elongate member 10 rapidly into the tissue at the target site. As shown in FIG. 9A, an apparatus of the invention includes an elongate member 10 having a sharpened tip 12, an electrode bundle 14, and a housing 16.

The apparatus of FIG. 9A is in its armed state and further includes an electrode actuating spring 59, an elongate member actuating spring 61, a pivoting electrode release pin 63, and a pivoting elongate member release pin 65. The release pin 65 is attached to the knob 67. When a user pulls the knob 67 away from the housing 16, the release pin 65 pivots, thereby releasing tension on the elongate member actuating spring 61 and rapidly advancing the elongate member 10 away from the housing 16 and into tissue at a target site in a body. The release of tension on the spring 61 causes the plate 71 to advance rapidly toward the electrode release pin 63. The protuberance 69 on the plate 71 strikes the release pin 63, thereby causing it to pivot and release tension on electrode actuating spring 59. As a result of the release of tension on the spring 59, the electrodes of electrode bundle 14 are rapidly advanced away from the distal end of the elongate member 10 and into tissue at a target site. The elongate member 10 and the electrodes of the electrode bundle 14 are therefore rapidly advanced in succession, with the release of tension on the elongate member actuating spring 61 resulting in release of tension on the electrode actuating spring 59 almost immediately thereafter.

Tension may be created on the electrode actuating spring 59 and the elongate member actuating spring 61 by pulling back on the slide tabs 75 and 77, respectively, both of which are shown in FIG. 9B. With respect to the electrode actuating spring 59, sliding the slide tab 77 toward the proximal end of the apparatus creates tension on the spring 59. The slide tab 77 is locked into place by the plate 73 resting against the electrode release pin 63. Similarly, tension is created on the elongate member actuating spring 61 by sliding the slide tab 75 toward the proximal end of the apparatus. The slide tab 75 is locked into place by the plate 71 resting against the elongate member release pin 65. The apparatus of FIG. 9C is shown in its unarmed state with the electrodes of the electrode bundle 14 in their deployed configuration.

In alternative embodiments, other devices for generating a force on the electrodes of the electrode bundle 14 and on the elongate member 10 may also be used to advance rapidly these portions of the apparatus of the invention. Such devices include, but are not limited to, motors, rubber bands, hydraulics, levers, lever and hammer configurations, and combustion/explosion devices. As used herein, "rapidly" means that the electrodes of the electrode bundle 14 are advanced at a rate of between about 30 cm/s and about $10^5$ cm/s, and that the elongate member 10 is advanced at a rate of between about 30 cm/s and about $10^5$ cm/s.

Figure 10:
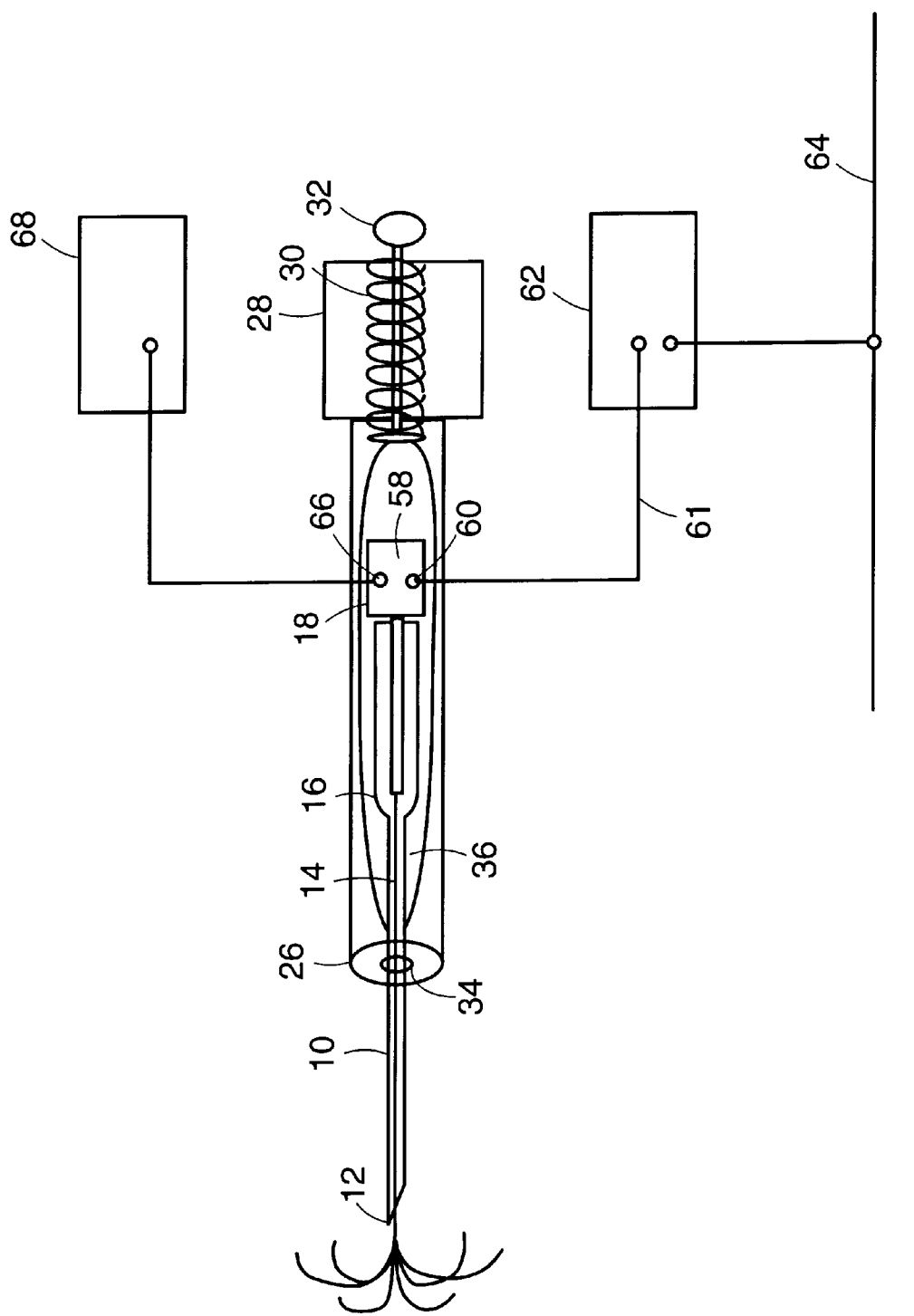
FIG. 10 is an illustration of an apparatus of the invention with an RF energy source and an impedance monitor for use in a monopolar fashion.

Another embodiment of the invention is shown in FIG. 10. In this embodiment, the electrode bundle 14 is shown in electrical communication via the pin connector 60 on the plunger 18 with the RF power supply 62. A wire 61 connects the RF power supply 62 to the pin connector 60 via the power supply connection opening 36 in the side of the cannula 26. The RF power supply 62 is any conventional electrosurgical power supply that operates within the RF range (i.e., 400 kHz to 1.2 MHz) with a conventional sinusoidal or non-sinusoidal wave form.

FIG. 10 shows an apparatus of the invention having a spring electrode actuator by way of example only. An apparatus of the invention having a pneumatic cylinder electrode actuator may also be used. In the embodiment containing a pneumatic cylinder electrode actuator, the RF power supply 62 is connected via the wire 61 to the pin connector 60 through power supply connection opening 58.

The embodiment of the invention in FIG. 10 is for monopolar operation. The RF power supply 62 is therefore also shown in electrical communication with the passive electrode 64. In operation, the passive electrode 64 is maintained external to the patient's body. In an alternative embodiment, the invention is operated in a bipolar fashion. As is apparent to those of ordinary skill in the art, operation of the apparatus of the invention in a bipolar fashion requires that a return circuit be integrated into the apparatus. This may be accomplished by, for example, including a return electrode in electrical communication with the RF power supply 62 within the electrode bundle 14. The return electrode may be covered with an insulative material.

In the illustration of the apparatus of the invention in FIG. 10, the electrode bundle 14 is also shown in electrical communication via the pin connector 66 with the impedance monitor 68. Increases in the impedance may be shown by a display on the impedance monitor 68. As tissue at a target site is subjected to RF energy and thereby ablated, the impedance of that tissue changes. By monitoring an impedance of tissue at the target site, a physician can determine the extent to which the tissue is ablated.

In one embodiment, the impedance monitor 68 and the RF power supply 62 are embodied as an integrated device. In this embodiment of the invention, the physician sets the power on the integrated device, and this power is used to fix the voltage applied to the electrodes of the electrode bundle 14. As the impedance of the tissue changes, the current supplied by the integrated device changes so as to maintain this fixed voltage. The integrated device monitors the impedance until a predetermined maximum impedance is reached, at which point the integrated device shuts itself off. This predetermined maximum impedance is the impedance which indicates that the tissue is ablated. Since the integrated device automatically shuts off when this maximum impedance is detected, the amount of current that is passed to surrounding healthy tissues is minimized.

Figure 11A:
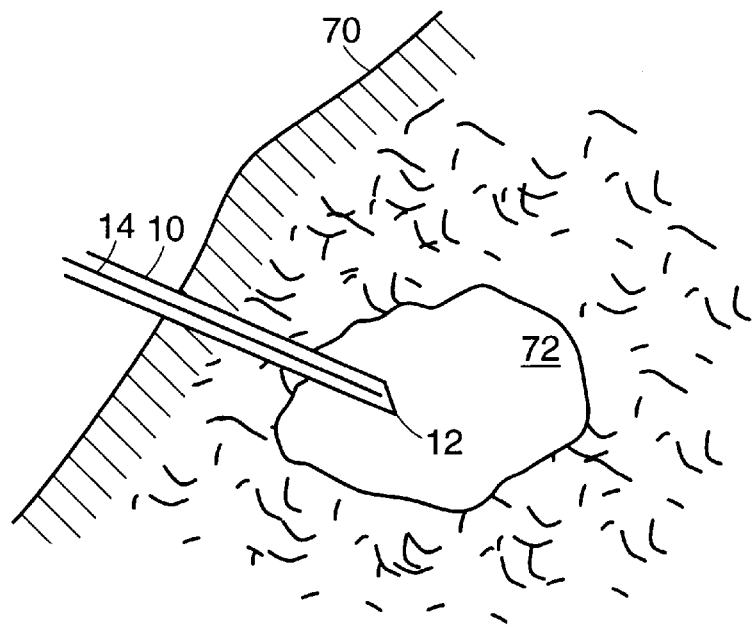
FIG. 11A is an illustration of an apparatus of the invention inserted into tissue to a target site.

Methods of the invention provide for the ablation of tissue using an apparatus of the invention. An apparatus of the invention, as described above, is provided, and the body tissue 70 is penetrated with the sharpened tip 12 of the elongate member 10 so as to advance the tip 12 to the target site 72, as shown in FIG. 11A. In one embodiment, the elongate member 10 is rapidly advanced so that the sharpened tip 12 penetrates the tissue at the target site 72. This method is particularly useful when attempting to ablate dense, fibrous tumors, such as breast tumors, which may move relative to the elongate member 10 if it is manually advanced to the target site 72. After the tip 12 is advanced to the target site 72, an access lumen from outside the patient's body, through the tissue, and to the target site 72 is created. The target site 72 may be located within the patient's body using any conventional imaging technique, such as ultrasonic scanning, magnetic resonance imaging (MRI), computer-assisted tomography (CAT), fluoroscopy, etc. Alternatively, an apparatus of the invention may have an elongate member coated with an echogenic coating, such as STS biopolymers or a plastic coating containing gas bubbles, so that the tip of the elongate member 10 can be properly positioned at the target site 72 using ultrasonic imaging techniques.

In an alternative embodiment, other devices may be used to access the target site 72 in lieu of penetrating with the sharpened tip 12. For example, a conventional sheath and obturator assembly may be used to create an access lumen through the tissue to the target site 72.

Figure 11B:
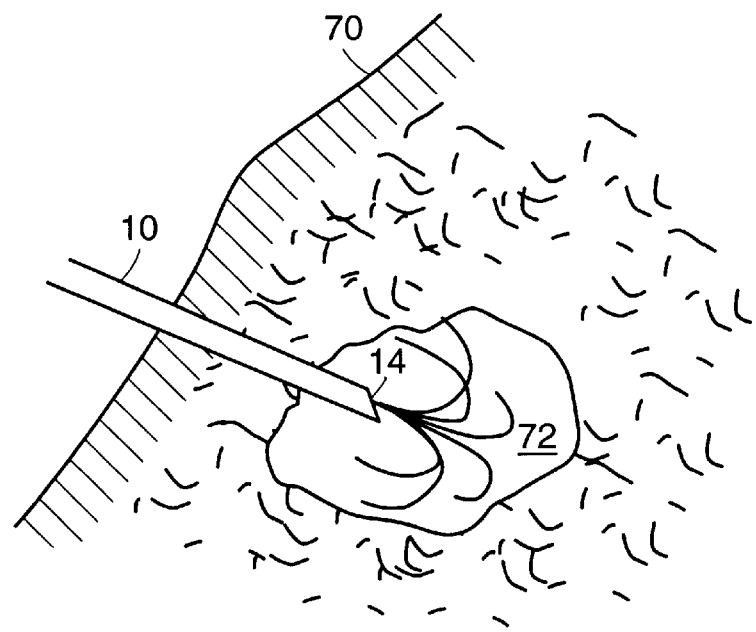
FIG. 11B is an illustration of the apparatus of FIG. 11A with the electrodes deployed into tissue at a target site.
Figure 12A:
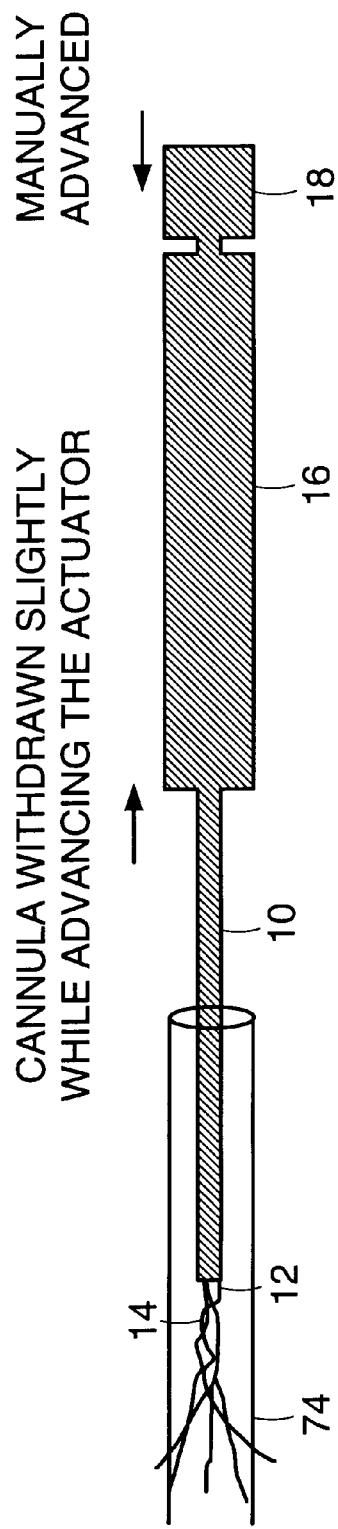
FIG. 12A is an illustration of an electrode array after being deployed into a surrounding material without rapid deployment.

Once the apparatus is positioned at the target site 72, the electrodes of the electrode bundle 14 are rapidly advanced into the tissue at the target site 72 so that the electrodes assume an outwardly everted configuration, as shown in FIG. 11B. Rapid advancement of the electrodes of the electrode bundle 14 from the distal end of the elongate member 10 ensures that electrodes of the electrode bundle 14 adopt the configuration shown in FIG. 11B. As shown in FIG. 12A, electrodes advanced without the use of an electrode actuator, as described above, often become bent or twisted and do not penetrate a surrounding material 74, or may penetrate, but in all cases fail to form an outwardly everted configuration within the penetrated tissue. Additionally, the device may move relative to the target site 72 and fail to penetrate tissue at the target site 72 without rapid advancement. Alternatively, the tissue at the target site 72 may move relative to the device, so that the electrodes do not penetrate the tissue at the target site 72.

Figure 12B:
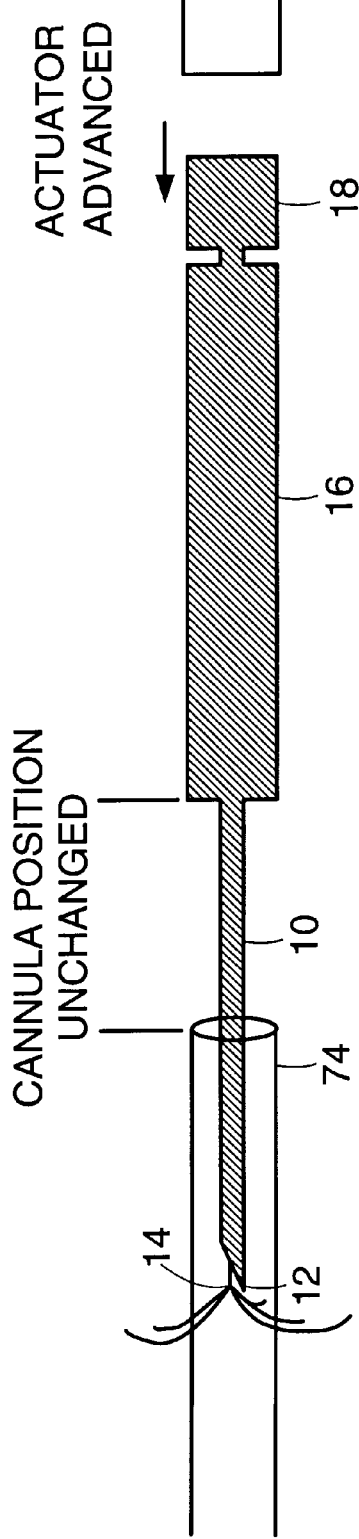
FIG. 12B is an illustration of the electrode array after being deployed into a surrounding material with rapid deployment.

With rapid advancement of the electrodes of the electrode bundle 14, however, the electrodes of the electrode bundle 14 penetrate the surrounding material 74 without the elongate member 10 moving relative to the target tissue, as shown in FIG. 12B. When rapidly advanced, the electrodes of the electrode bundle 14 assume the outwardly everted configuration within the tissue, as shown in FIG. 12B. This outwardly everted configuration permits the ablation of larger treatment volumes of tissue at the target site. Finally, with rapid advancement of the electrodes of the electrode bundle 14, the tissue at the target site is less likely to move relative to the device, and is therefore more likely to be penetrated by the electrodes.

After the electrodes of the electrode bundle 14 are in place within the target site 72, the tissue at the target site 72 is ablated. In one embodiment, the tissue is ablated by delivering RF energy to the target site via the electrodes of the electrode bundle 14. The RF energy is generated by the RF power source 62, as described above. In one embodiment, the power generated by the RF power source 62 is incrementally increased at regular intervals as the tissue at the target site 72 is ablated. For example, the power is increased 10 W/min. during the ablation procedure.

In one embodiment of the invention, the impedance of the tissue at the target site is monitored during ablation of tissue at the target site. The impedance is monitored by an impedance monitor 68, as described above. In one embodiment, a voltage is fixed when the ablation procedure is initiated, and the current is changed as the impedance changes so as to maintain this fixed voltage during the ablation procedure. When the impedance of the tissue at the target site reaches a predetermined maximum, the RF power source 62 automatically shuts down. This maximum impedance indicates that the tissue at the target site has been ablated.

In an alternative method, a second round of ablation is performed at a reduced power level. After the RF power source 62 has automatically shut down due to the tissue reaching a predetermined maximum impedance level, the RF power source 62 is restarted at approximately 75% of the power initially used in the first round of ablation. For example, if power during the first round of ablation was initially set at 40 W, power for the second round of ablation is set at 30 W. The ablation is allowed to continue at this reduced power setting until a second predetermined maximum impedance is reached and the RF power source 62 automatically shuts down again.

Upon completion of the ablation procedure, the electrodes are retracted into the elongate member 10 by pulling the plunger 18 away from the housing 16, and the apparatus is removed from the patient's body. In one embodiment, the elongate member 10 has an external surface that is covered with an insulating material, except for a 1 cm segment at the distal end of the elongate member 10. This exposed distal end of the elongate member 10 allows for the cauterization of the access lumen as the apparatus is removed from the patient's body.

Apparatus and methods of the invention therefore provide for the ablation of tissue. Larger treatment volumes are consistently ablated using apparatus and methods of the invention due to the outwardly everted configuration of the electrodes in the tissue. The outwardly everted configuration of the electrodes is ensured by the rapid advancement of the electrodes beyond the distal end of the device and into the tissue. With this rapid advancement, the incidence of bending or twisting of the electrodes as they enter tissue at a target site is reduced or eliminated.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. An apparatus for tissue ablation, comprising:
    (a) an elongate member including a lumen and a distal end wherein said distal end of said elongate member comprises a sharpened tip for penetrating tissue;
    (b) at least two retractable electrodes housed within said elongate member and advanceable beyond said distal end of said elongate member and into tissue to a target site within the tissue;
    (c) an electrode actuator for rapidly advancing said electrodes beyond said distal end of said elongate member and into tissue to the target site so that said electrodes assume an outwardly everted configuration when advanced beyond said distal end of said elongate member and into the tissue; and
    (d) an elongate member actuator for rapidly advancing said elongate member so that said sharpened tip penetrates tissue at the target site.

2. The apparatus of claim 1, wherein said elongate member actuator comprises a spring.

3. A method of ablating tissue, comprising the steps of:
    (a) providing a medical device, comprising
        (i) an elongate member including a lumen and a distal end, wherein said distal end comprises a sharpened tip for penetrating tissue;
        (ii) at least two retractable electrodes housed within said elongate member and advanceable beyond said distal end of said elongate member and into tissue to a target site within the tissue;
        (iii) an electrode actuator for rapidly advancing said electrodes beyond said distal end of said elongate member and into tissue to the target site so that said electrodes assume an outwardly everted configuration when advanced beyond said distal end of said elongate member and into tissue; and
        (iv) an elongate member actuator for rapidly advancing said sharpened tip into tissue to the target site
    (b) rapidly advancing said sharpened tip into tissue to said target site;
    (c) rapidly advancing said electrodes from said distal end of said elongate member and into tissue to the target site so that said electrodes assume an outwardly everted configuration; and
    (d) ablating tissue at the target site with said electrodes.

* * * * *